United States Patent [19]

Paris

[11] Patent Number: 4,911,693
[45] Date of Patent: Mar. 27, 1990

[54] HYPODERMIC SYRINGE NEEDLE GUARD

[76] Inventor: Frassetti R. Paris, 1378 Dahill Rd., Brooklyn, N.Y. 11204

[21] Appl. No.: 258,714

[22] Filed: Oct. 17, 1988

[51] Int. Cl.⁴ .............................................. A61M 5/32
[52] U.S. Cl. .................................. 604/192; 604/198; 604/263
[58] Field of Search ............... 604/198, 110, 187, 263, 604/192

[56] References Cited

U.S. PATENT DOCUMENTS

| | | | |
|---|---|---|---|
| 4,664,654 | 5/1987 | Strauss | 604/198 |
| 4,747,831 | 5/1988 | Kulli | 604/110 |
| 4,813,940 | 3/1989 | Parry | 604/198 |

*Primary Examiner*—John D. Yasko
*Attorney, Agent, or Firm*—James & Franklin

[57] ABSTRACT

A first cylindrically shaped part surrounds and is fixed to the needle base which is mounted on the forward end of the syringe body. A second cylindrical part is mounted within the first part for axial movement between a forward position where the needle is surrounded for protection of the needle prior to mounting and between injections and a position in which the needle is exposed during an injection. A spring urges the second part towards the forward position. Locking elements are provided for permanently locking the second part in a third, axially spaced position to protect the needle after it has been discarded. Prior to and between injections, the second part may be non-permanently locked in the forward position by rotating it relative to the first part.

18 Claims, 2 Drawing Sheets

HYPODERMIC SYRINGE NEEDLE GUARD

The present invention relates to a guard for the needle of a hypodermic syringe or the like and more particularly to a needle guard designed to surround and protect the needle prior to mounting, between injections and after it has been discarded.

Workers in the medical and dental fields have long been aware of the dangers of catching communicable diseases from contact with the exposed tip of a contaminated hypodermic syringe needle. In addition, there is the danger of physical injury which can result from accidental contact with the sharp tip of an exposed needle.

More recently, the public has become accutely aware of the presence of communicable diseases such as AIDS or Hepatitis in medical waste, specifically discarded hypodermic needles. This danger is heightened when contaminated needles are not properly discarded and end up in the environment. For example, there have been cases of medical waste dumpted off shore where the needles have washed up on public beaches.

Accordingly, there is a great need for a simple and inexpensive guard which can be provided, preferably in conjunction with a disposable needle, in a sterilized container. The guard should protect the needle tip from exposure prior to and during the time the needle is mounted on the syringe and between injections, if the needle is employed to give multiple injections. In addition, the guard should protect the needle after it has been removed from the syringe in a permanent manner, that is, in a manner which prevents exposure of the needle, except if the guard is physically destroyed.

In the past, there have been a number of attempts to design needle guards with varying degrees of success. However, there is no needle guard which fulfills the above requirements and at the same time is sufficiently simple and inexpensive to permit wide spread commercial usage.

It is therefor, a prime object of the present invention to provide a hypodermic syringe needle guard which protects the tip of the needle from exposure prior to and during mounting of the needle, between injections and after the needle has been discarded.

It is another object of the present invention to provide a hypodermic syringe needle guard which fulfills all of the above mentioned requirements and is simple in construction and inexpensive to produce.

It is another object of the present invention to provide a hypodermic syringe needle guard which can be permanently locked in a position wherein the needle tip is protected.

In accordance with one aspect of the present invention, a needle guard is provided for use with a syringe of the type having a cylindrical body with a needle having a base mounted to and extending from the forward end thereof. The needle guard includes a first part which is adapted to be fixedly mounted for movement to the base and hence non-moveably mounted to the syringe body. A second part is mounted for movement relative to the first part between the first position wherein the needle tip is unexposed and a second position wherein the needle tip is exposed. Means are provided for urging the second part towards the first position. Means are also provided for permanently locking the second part in a position wherein the needle tip is unexposed.

The second means is moveable to a third position. The permanent locking means is effective to permanently lock the second part in the third position. The third position is preferably spaced from the first and second positions.

The second part is mounted for movement within the first position between a non-permanently locked location and a non-locked location. Means are provided for non-permanently locking the second part in the non-permanently locked position. The non-permanently locking means comprises a protrusion on the second part and a substantially "T" shaped slot on the first part. Preferably, the non-permanently locked location is rotationally off-set from the non-locked location.

The permanent locking means comprises means associated with the second part for engaging the first part in a non-releaseable fashion. The engaging means includes a resilient element normally extending radially from the first part and a recess on the first part adapted to receive the radially extending element when the second part is in the third position.

The first part includes a surface adapted to cam the radially extending element to a position which permits the second part to move towards the third position. The engaging element cooperates with the recess in the first part to prevent the second part from moving from the third position.

The second part includes a substantially tubular member surrounding the needle. The needle includes a base which is mounted to the forward end of the syringe body. The first part substantially surrounds the needle base and is spaced therefrom defining a recess therebetween into which the second part is received.

In accordance with another aspect of the present invention, a hypodermic needle for use with a syringe is provided. The needle has a base and a shaft with a tip. Guard means is provided for the needle. The guard means includes a first part fixedly mounted to the base. A second part is mounted for movement relative to the first part between a first position wherein the needle tip is unexposed and a second position wherein the needle tip is unexposed and a second position wherein the needle tip is exposed. Means are provided for urging the second part towards the first position. Means are also provided for permanently locking the second part in a position wherein the needle is unexposed.

To these and such other objects which may hereinafter appear the present invention relates to a hypodermic syringe needle guard as described in detail in the following specification, and recited in the annexed claims, wherein like numerals refer to like parts and in which:

Figure 5:
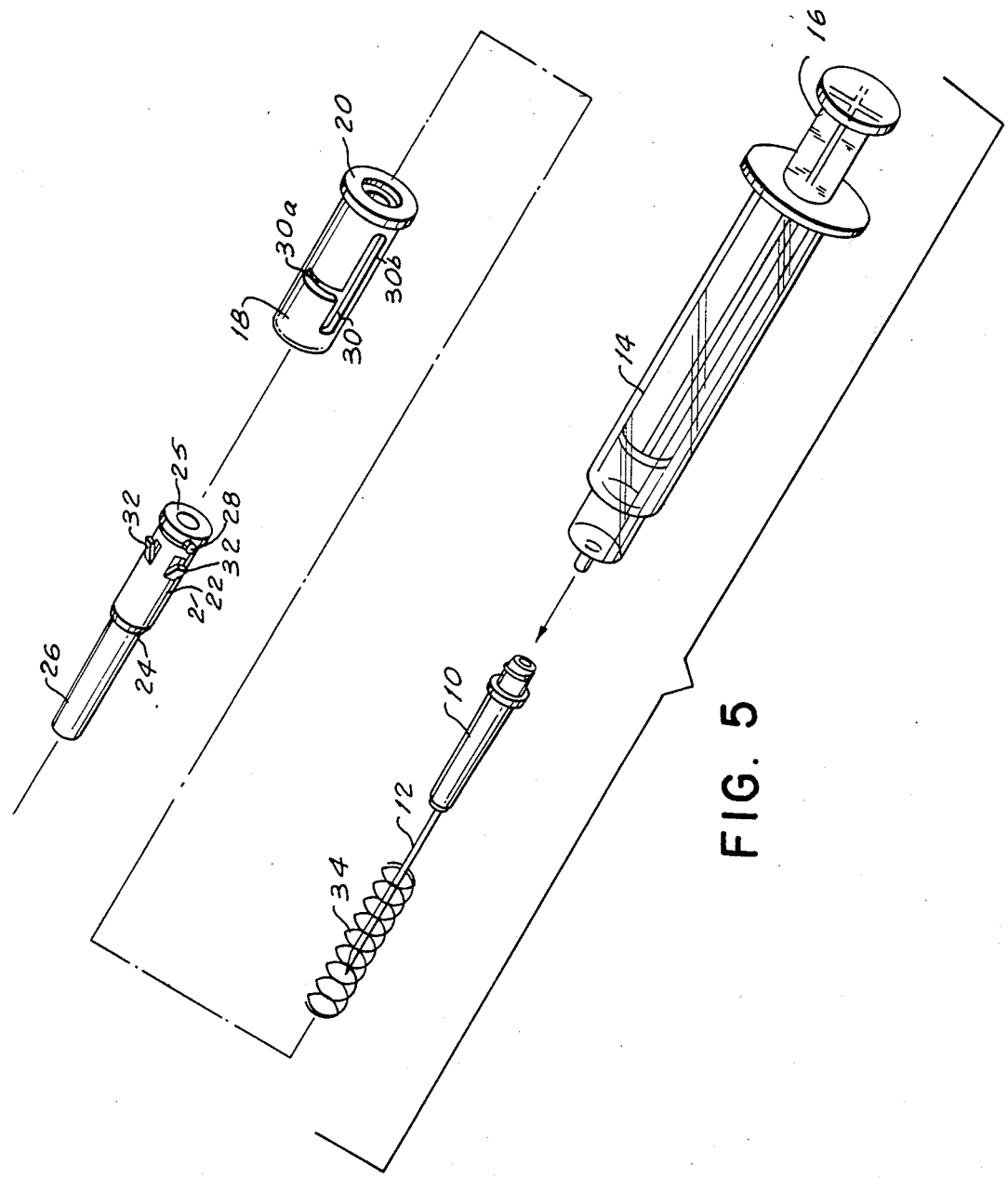
FIG. 5 is an exploded isometric view of a syringe and a needle guard of the present invention.
Figure 1:
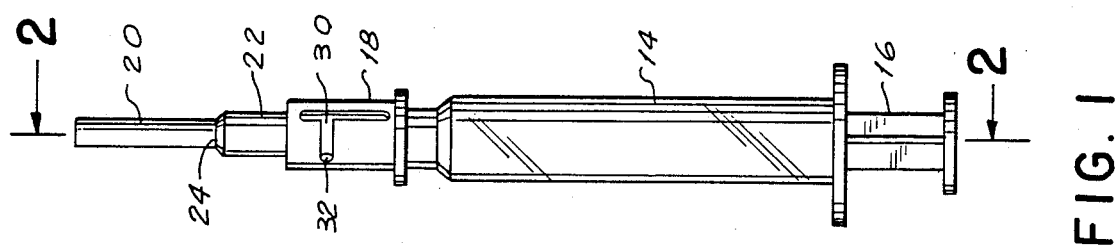
FIG. 1 is a plan view of a hypodermic syringe with a needle and the needle guard of the present invention mounted thereon.

As can be best seen in FIG. 5, the needle guard of the present invention comprises three simple parts, two of which may be made of plastic by injection molding and the third of which is a conventional spring. The parts are designed to be mounted on a hypodermic needle, preferably as a portion of a single sterile package.

The needle, which is conventional, includes a plastic base 10 from which extends a hollow metal needle 12, with a sharp forward tip. Base 10 is designed to be mounted to the forward end of a hypodermic syringe in a conventional manner. The syringe includes a cylindrical body 14 and a plunger 16.

The guard itself includes a first part 18 which has substantially hollow cylindrical or tubular configuration with a radially extending annular rim 20 to facilitate gripping. Within part 18 is received a portion of a second hollow, cylindrical or tubular part 24. Part 24 is received within part 18 in a moveable manner as will be described in detail in conjunction with FIGS. 2, 3 and 4.

Part 24 has a rear larger diameter section 22 and a forward smaller diameter section 26. The interior surface of part 24 has a shape which roughly corresponds to the outer contours of base 10 and needle 12.

Section 22 of part 24 is provided, at the rear portion thereof, with an annular rim 25 upon which is mounted a radially extending protrusion 28 designed to be received within a "T" shaped slot 30 on part 18. Section 22 also has a plurality of radially extending resilient elements 32 which form a portion of a permanent locking means described below.

A spring 34 is provided to be received within the recess formed between part 18 and part 24 with one end thereof abutting the rim 25. This can be best seen with references to FIGS. 2, 3 and 4.

Figure 2:
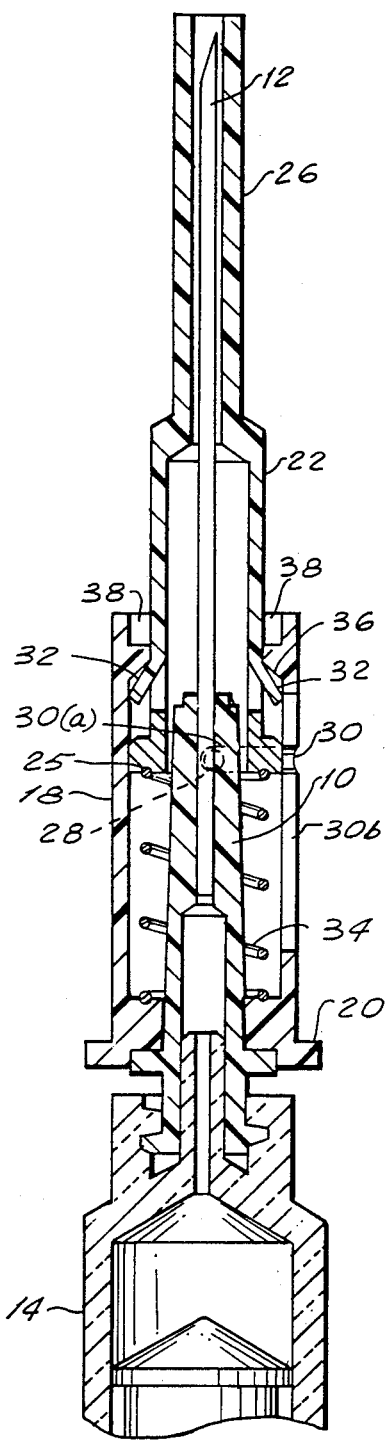
FIG. 2 is an enlarged cross-sectional view of the front portion of the syringe illustrated in FIG. 1 with the needle guard in the forward position.

FIG. 2 depicts the needle guard in its unexposed (forward) position where Section 26 of part 24 surrounds the tip of needle 12 such that it cannot come in contact with the skin. The guard is shown in the non-permanently locked location within the unexposed position. At this location, the guard, and particularly part 24 thereof, cannot be moved axially because of the bayonet type engagement between protrusion 28 on part 24 and the circumferential portion 30a of slot 30 on part 18. This is the state in which the guard and needle assembly is provided by the manufacturer, preferably in a sterile package. The package is opened and the needle base 10 is friction fitted over the forward portion of syringe body 14 by gripping the exterior surface of part 18 and particularly rim 20. The needle tip is never exposed prior to or during the mounting of the needle and guard assembly on the syringe.

The needle guard will remain in the non-permanently locked location of the unexposed position until the time that an injection is to be performed. At that time, the user rotates part 24 relative to part 18 approximately 90 degrees such that protrusion 32 travels along circumferential portion 30a of slot 30 in part 18 until it reaches the axially extending portion 30b thereof. This is the non-locked location of the unexposed position. Part 24 is now urged toward the unexposed position only by spring 34.

Figure 3:
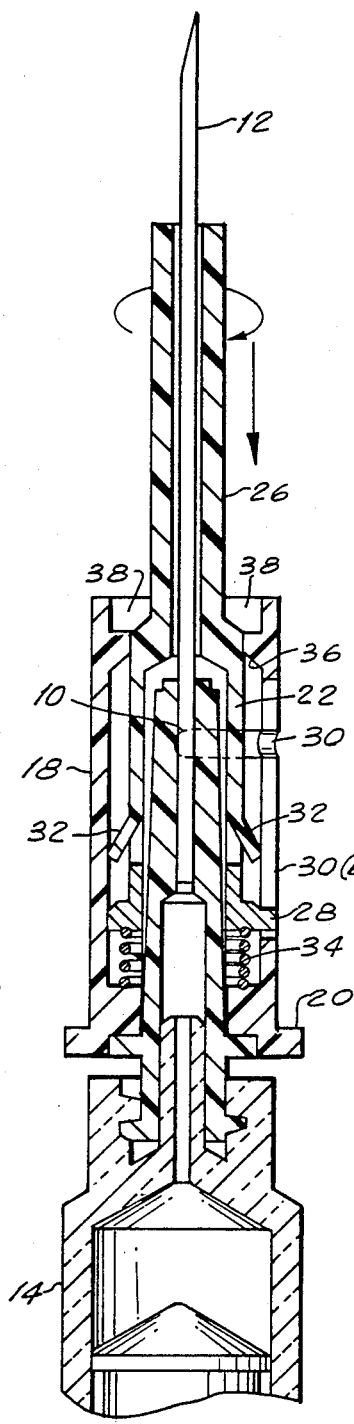
FIG. 3 is a view similar to FIG. 2 but showing the needle guard in the injection position.

When the forward end of the guard is gently pressed against the skin as an injection is performed, part 24 moves against the urging of spring 34 within part 18 towards syringe body 14 as protrusion 32 rides rearwardly along the axially extending section 30b of slot 30. Part 24 can be moved with respect to part 18 until protrusion 32 reaches the bottom of the axially extending section 30b of slot 30, as depicted in FIG. 3.

When the needle 12 is withdrawn from the skin at the end of the injection, spring 34 will cause part 24 to move away from the syringe body and once again reach the non-locked location wherein the needle is unexposed. As long as protrusion 28 remains in section 30b of slot 30, part 24 can move freely forwardly and rearwardly against the urging of spring 34 in an axial direction relative to part 18. If the needle is used to give multiple injections, part 24 will surround and protect the tip of needle 12 between the injections. It will not interfere with the multiple use of the needle. If desired, between injections, part 24 can be rotated 90 degrees relative to part 18. This in the non-permanently locked position such will cause it to be that the needle tip cannot be exposed accidentally.

Figure 4:
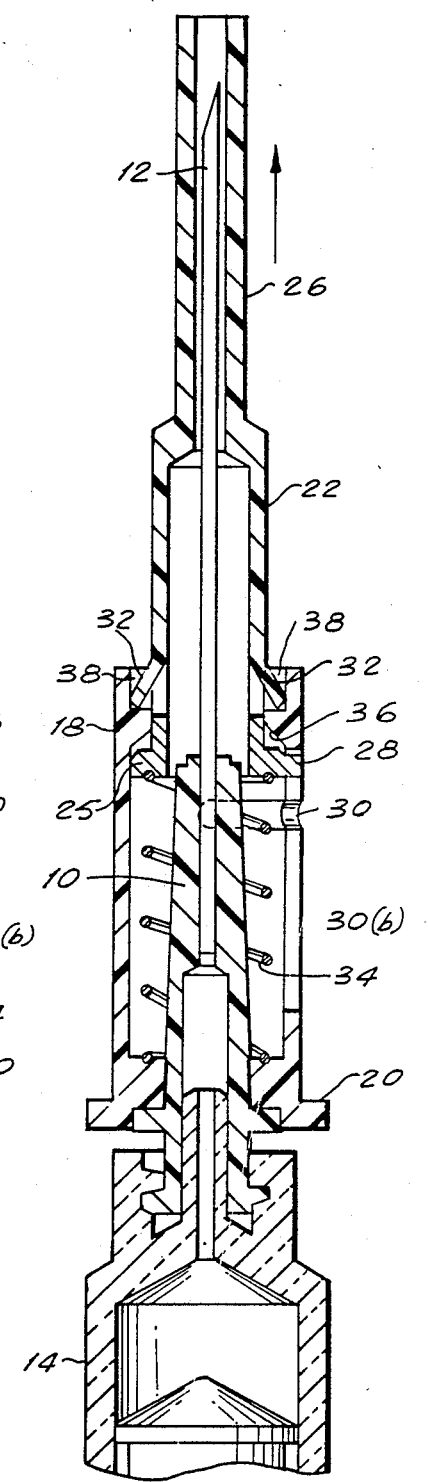
FIG. 4 is a view similar to FIG. 2 but showing the needle guard in the permanently locked position.

When the needle is ready to be discarded, part 24 is displayed from part 18 to a third, permanently locked, axial position as seen in FIG. 4. Thereafter, the needle and guard assembly can be removed from the syringe and discarded as a unit. In the locked position, the tip of needle 12 is permanently surrounded and protected by section 26 of part 24 and cannot be exposed unless the needle guard is dismantled and/or destroyed.

As best seen in FIG. 4, the forward position of the interior surface of part 18 is provided with an annular, inwardly inclined surface portion 36. The radially extending elements 32 from section 22 of part 24 will be situated adjacent surface 36 when part 24 is in the forward, unexposed position, whether at the non-permanently locked or non-locked location. As part 24 is moved away from syringe body 14 towards the permanently locked position, surface 36 serves to cam resilient elements 32 inwardly to permit same to pass into an annular recess 38 at the forward end of part 18. When this occurs, resilient elements 32 move radially outwardly to their original expanded positions and lodge within recess 38, as can best be appreciated from FIG. 4. Part 24 cannot move axially relative to part 18 and hence the tip of needle 12 cannot become accidentally exposed. Part 24 cannot move towards part 18 because of elements 32 lodged within recess 38. Part 24 cannot move away from part 18 because of rim 25 which abuts 36 and protrusion 28 which abuts the forward edge of slot 30 and thus prevents the bottom rim and particularly the protrusion 32 from movement in this direction. Accordingly, the needle guard is permanently locked in a position wherein the needle is protected and the unit can be disposed of without danger after removal.

It is preferable to design the guard such that less force is required to move part 24 to the permanently locked position than is necessary to remove base 10 from the syringe. This should insure locking of the guard as the needle is removed from the syringe.

It can now be appreciated that the present invention relates to a needle guard which completely protects against accidental contact with the needle tip before it is mounted to the syringe, during the mounting procedure, between injections, as the needle is removed from the syringe and after it is disposed of. The needle guard has a relatively simple structure and can be produced relatively inexpensively with plastic injection molded parts. Moreover, the needle guard of the present invention can be provided inconjunction with the needle as a unit in a single, sterile package.

While only a single preferred embodiment of the present invention has been disclosed for purposes of illustration, it is obvious that many variations and modifications can be made thereto. It is intended to cover all of these variations and modifications which fall within the scope of the present invention as defined by the following claims:

I claim:

1. A needle guard for use with a syringe of the type having a cylindrical body with an axis and a needle extending from and fixably mounted on the forward end thereof, said guard comprising a first part adapted to be non-moveably mounted on said body, a second part mounted for movement relative to said first part between a first axial position wherein the needle tip is unexposed and wherein said second part can be moved circumfrentially to a non-permanently locked position, a second axial position wherein the needle tip is exposed and a third axial position wherein the needle tip is unexposed, means for urging said second part towards said first axial position and means for permanently locking said second part in said third axial position, said locking means comprising resilient means having a portion normally extending radially from said second part and a recess on said first part adapted to receive said radially extending portion in a non-releasable fashion when said second part is in said third axial position.

2. The guard of claim 1 wherein said first part has a protrusion, said second part has a slot with a substantially axial portion and a substantially circumferential portion and said potrusion is received within said slot.

3. The guard of claim 2 wherein said protrusion is located proximate one end of said axial portion when said second part is in said second axial position and proximate the other end of said axial portion when said second part is in said third axial position.

4. The guard of claim 2 wherein said protrusion is moveable within said circumfrentially extending portion when said second part is in said first axial position between said axial directed portion within which said second part is moveable in an axial direction and said circumfrentially extending portion wherein said second part is not moveable in an axial direction.

5. The guard of claim 1 wherein said third position is spaced from said first and second positions.

6. The guard of claim 1 wherein said second part is mounted for movement within said first position between a non-permanently locked location and a non-locked location.

7. The guard of claim 6 further comprising means for non-permanently locking said second part in said non-permanently locked position.

8. The guard of claim 7 wherein said means for non-permanently locking said second part comprises a protrusion on said second part and a substantially "T" shaped slot on said first part into which said protrusion is removably received.

9. The guard of claim 6 wherein said non-permanently locked location is rotationally off-set from said non-locked location.

10. The guard of claim 1 wherein said first part comprises a surface adapted to cam said radially extending element to a position which permits said second part to move toward said third position.

11. The guard of claim 1 wherein said radially extending element portion cooperates with said recess to prevent said second part from moving from said third position.

12. The guard of claim 1 wherein said second part comprises a substantially tubular member surrounding the needle.

13. The guard of claim 1 wherein the needle includes a base adapted to be mounted on said syringe body and wherein said first part is fixedly mounted to said base.

14. The guard of claim 13 wherein said first part substantially surrounds the needle base and is spaced therefrom defining a recess therebetween into which said second part is received.

15. A hypodermic needle adapted to be fixably mounted on a syringe, the needle comprising a base and a shaft with a tip and guard means for the needle comprising a first part fixably mounted to a base, a second part mounted for movement relative to said first part between a first axial position where the needle tip is unexposed and within which said second part can be moved circumfrentially with respect to said first part to a non-permanently locked position, a second axial position wherein the needle tip is exposed and a third axial position wherein the needle tip is unexposed and the first part is permanently locked, means for urging said second part towards said first axial position and means for permanently locking said second part in said third axial position, said locking means comprising a resilient element having a portion normally extending radially from said second part and a recess on said first part adapted to receive said radially extending portion in a non-releasable fashion when said second part is in said third axial position.

16. The needle of claim 15 wherein said second part is mounted for movement within said first position between a non-permanently locked location and a non-locked location.

17. The needle of claim 16 further comprising means for non-permanently locking said second part in said non-permanently locked location.

18. The needle of claim 17 wherein said means for non-permanently locking said second part comprises a protrusion on said second part and a substantially "T" shaped slot on said first part into which said protrusion is received.

* * * * *